United States Patent [19]

Pierce et al.

[11] Patent Number: 4,820,300
[45] Date of Patent: Apr. 11, 1989

[54] ARTIFICIAL HEART

[75] Inventors: William S. Pierce, Harrisburg; Gerson Rosenberg, Lebanon, both of Pa.

[73] Assignee: Research Corporation Technologies, Inc., Tucson, Ariz.

[21] Appl. No.: 56,576

[22] Filed: Jun. 1, 1987

Related U.S. Application Data

[63] Continuation-in-part of Ser. No. 747,096, Jun. 20, 1985, abandoned.

[51] Int. Cl.[4] .............................................. A61F 2/22
[52] U.S. Cl. ..................................................... 623/3
[58] Field of Search ........................................... 623/3

[56] References Cited

U.S. PATENT DOCUMENTS

| | | |
|---|---|---|
| 3,048,165 | 8/1962 | Norton . |
| 3,568,214 | 3/1971 | Schmied . |
| 3,720,485 | 3/1973 | Holman, Jr. . |
| 3,755,825 | 9/1973 | DeBakey et al. . |
| 3,874,002 | 4/1975 | Kurpanek . |
| 4,162,543 | 7/1979 | Shumakov et al. . |
| 4,310,930 | 1/1982 | Goldowsky . |
| 4,375,941 | 3/1983 | Child . |
| 4,376,312 | 3/1983 | Robinson et al. . |
| 4,381,567 | 5/1983 | Robinson et al. . |
| 4,389,737 | 6/1983 | Robinson et al. . |
| 4,397,049 | 8/1983 | Robinson et al. . |
| 4,427,470 | 1/1984 | Kolff ........................................ 623/3 |
| 4,468,177 | 8/1984 | Strimling . |
| 4,547,411 | 6/1985 | Strimling ................................ 623/3 |
| 4,623,350 | 11/1986 | Lapeyre ................................. 623/3 |
| 4,693,714 | 9/1987 | Lundback ............................... 623/3 |

OTHER PUBLICATIONS

Rosenberg, et al., An Electric Motor Driven Total Artificial Heart, IEEE Frontiers of Engineering and Health Care, 1982.

Primary Examiner—Richard J. Apley
Assistant Examiner—James Prizant
Attorney, Agent, or Firm—Scully, Scott, Murphy & Presser

[57] ABSTRACT

A totally implantable artificial heart that utilizes a fluid displaced from the left blood pump to power the right blood pump. The left blood pump is a sac-type pump powered by an electric motor that, when contracting and expanding, displaces a volume of fluid in a fluid chamber within the left pump housing. The fluid is displaced through a fluid line connecting the right blood pump, which is a pneumatically operated sac-type or rotary-type pump. The artificial heart permits spatial separation of the left and right blood pumps within the chest of the patient for ease in implantation.

30 Claims, 5 Drawing Sheets

ARTIFICIAL HEART

This patent application is a continuation-in-part application of Ser. No. 747,096, filed June 20, 1985, now abandoned in favor of the present application.

BACKGROUND OF THE INVENTION

1. Field of the Invention

This invention relates to an artificial heart and, more particularly, a completely implantable artificial heart.

2. Description of the Prior Art

The development of an artificial heart to replace the function of a diseased human heart is an important goal for medical science. The principal deficiencies of the prior art artificial hearts include the bulky size and weight of the devices and the high power required to operate them. A compact, energy efficient artificial heart has the potential of helping thousands of persons with severe heart disease.

At present, there are several types of artificial hearts that are under development. In one design, a hydraulic fluid is pumped to compress a valved blood sac of the left blood pump. The pump then reverses and the hydraulic fluid is directed to compress the sac of the right blood pump. The high speed required by the hydraulic fluid pump, and the rapid reversing, may place excessive forces on the bearings of the pump motor. Moreover, no suitable control system has been developed.

One example of a hydraulic pump for an artificial heart is shown in U.S. Pat. No. 3,048,165, issued to Norton. In the U.S. Pat. No. 3,048,165, the blood sacs are cyclically contracted and expanded by several magnetically operated diaphragms that force the hydraulic fluid into the chamber containing the sacs. Each diaphragm is attached to a plunger and gear mechanism that meshes with a sun gear so that the movement of one pump causes the other pumps to move. The wear on the numerous moving parts may reduce the reliability of the device.

In a second design, the two valve blood pumps are located on either side of a motor activated system. Pusher plates alternately cause pumping in the left blood pump and then the right blood pump.

A similar system is shown in U.S. Pat. No. 4,310,930 issued to Goldowsky. An oscillating vane alternately forces blood out of the left and right blood chambers Special valves are provided that permit blood to leak back into the right chamber while blood is being pumped out of that chamber. The valve system is an energy inefficient means for compensating for the requirement that the right side of the heart pumps less blood than the left side.

In a third system, two separate and complete motor driven blood pumps are implanted to provide circulation. This system is also bulky, and it is therefore difficult to implant within the chest. Thus, there is a need for a completely implantable artificial heart system that is compact in weight and size for ease in implantation.

SUMMARY OF THE INVENTION

An object of the present invention is to provide an artificial heart wherein the right blood pump is powered by a fluid displaced from the left blood pump, thereby decreasing the size and the weight of the artificial heart.

A further object of the present invention is to provide an artificial heart that permits spatial separation between the left and right blood pumps in the body for ease in implantation within the chest.

In accordance with the present invention, an artificial heart is provided having a left blood pump that is an enclosed, valved, sac-type pump and a right blood pump which may be of a valved sac or rotary type pump. The left blood pump is powered by a motion translating means that, during the pumping action, displaces fluid located behind the sac of the left blood pump. A fluid line connecting the left blood pump to the right blood pump transfers the displaced gas to the right blood pump to actuate the pumping means of the right blood pump for expelling and receiving blood therein.

The right blood pump is within the low pressure lung circuit and is required to perform only one quarter to one fifth the amount of work as the left blood pump, which is connected within the high pressure systemic circuit. Thus, the right blood pump can easily be run from the displaced fluid from the left blood pump.

The left and right blood pumps of the present invention are spatially separated from each other, being interconnected by the fluid line. The physical separation between the pumps provides a high degree of flexibility for the surgeon implanting the heart. There may be inadequate space within the chest of the patient to accommodate the size of an artificial heart having both left and right pumps in a single unit. The present invention solves this problem by allowing one pump to be placed in the chest while the other pump is placed in the abdomen.

Moreover, there may be space in the chest but not a sufficient amount in one area to accept a single unit device. In this instance, the present invention allows the surgeon the possibility of placing one pump in, for example, the upper left quadrant of the chest, and the other pump in the lower right quadrant. Thus, the artificial heart of the present invention facilitates implantation, in addition to being energy efficient.

DETAILED DESCRIPTION OF THE INVENTION

Figure 1:
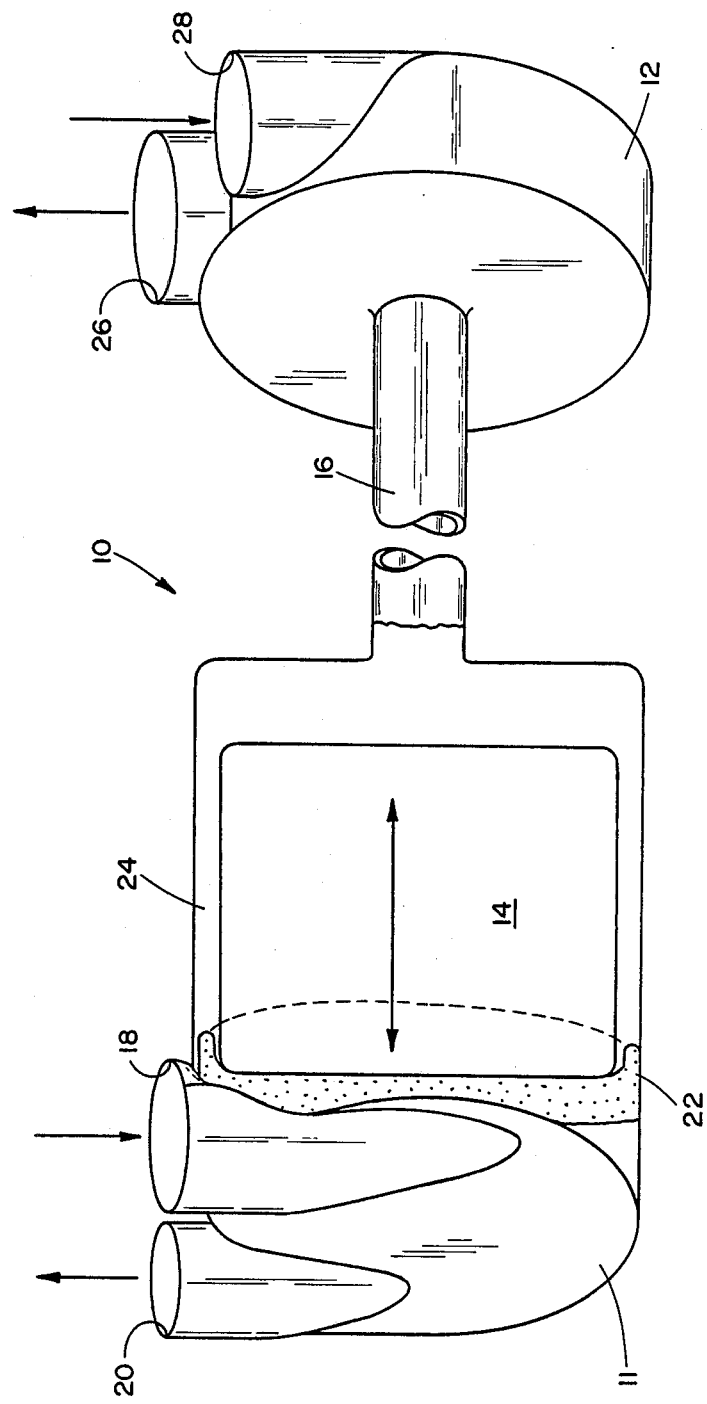
FIG. 1 is a schematic diagram of the artificial heart of the present invention.

Referring now to the drawings, FIG. 1 is a schematic representation, partially in cross-section, of the artificial heart 10 including a left blood pump 11 and a right blood pump 12. A motion translating means 14 actuates the left blood pump 11. A fluid line 16 connects the left blood pump 11 to the right blood pump 12. The left blood pump 11 includes an inlet port 18, an outlet port 20, and a blood sac 22. A fluid chamber 24 is located within the left blood pump 11 adjacent the sac 22. The fluid chamber 24 contains a fluid that is displaced through the fluid line 16 to the right blood pump 12.

The motion translating means 14 alternately contracts and expands the blood sac 22 for expelling blood through the port 20 and receiving blood through the port 18. As shown in FIG. 1, the blood sac 22 is contracted by the translating means 14. The expanded position of the sac 22 is shown in phantom. The contracting and expanding of the left blood pump blood sac 22 cyclically displaces the fluid in the left blood pump 11 and propels the fluid through the fluid line 16 into the right blood pump 12. The displaced fluid from the left blood pump 11 actuates the pumping means of the right blood pump 12 to alternately expel blood through an outlet port 26 and receive blood through an inlet port 28 of the right blood pump 12.

The fluid displaced between the left and right pumps may be a gas, liquid or some combination thereof. The preferred fluid is an inert gas such as $SF_6$, He, Ar or some blend of these.

Figure 2:
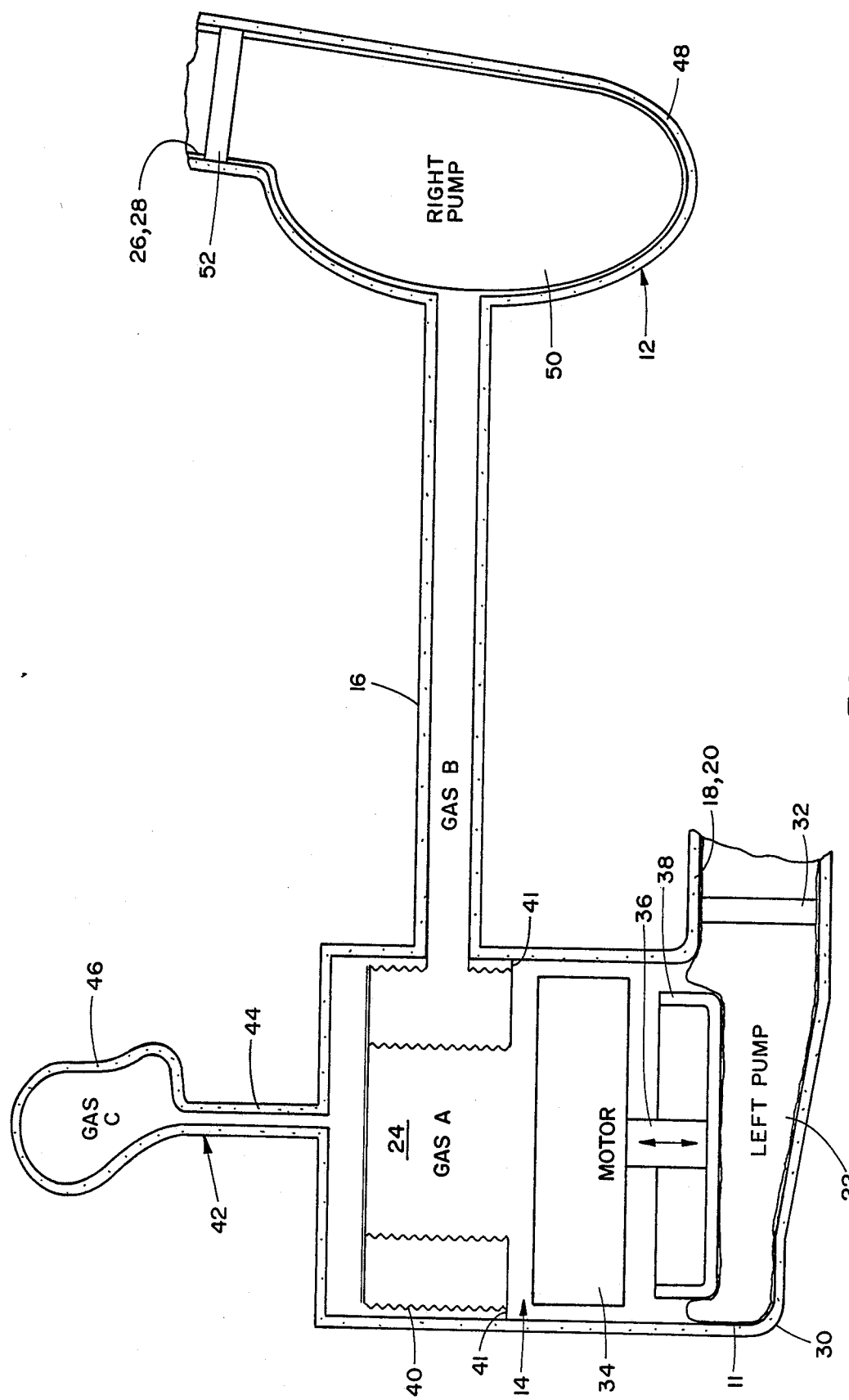
FIG. 2 is a schematic diagram of one embodiment of the artificial heart wherein the motion translating means includes a bellows.

FIG. 2 shows, in cross section, one embodiment of the present invention wherein the left blood pump 11 and the motion translating means 14 are enclosed in a housing 30. In the cross-sectional views of the remaining FIGS. 2-5, only one of the inlet and outlet ports for each pump 11 and 12 is shown, but it is understood that each pump includes both ports. Each of the inlet and outlet ports 18 and 20 includes a valve 32 to control the flow of blood through the ports. The motion translating means 14 includes an electric motor 34 having an output shaft 36. The electric motor 34 should preferably be of a brushless type, and may be either DC or AC. A pusher plate 38 is attached to the output shaft 36 and is in contact with the blood sac 22. The motor 34 causes the output shaft 36 and the pusher plate 38 to reciprocate away from and back towards the motor 34, thereby causing the pusher plate 38 to contract the blood sac 22 for ejecting blood and to expand the blood sac 22 for receiving blood.

A gas chamber 24 contains a volume of gas A. Located within the gas chamber 24 is a bellows 40 containing a second volume of gas B. The gas chamber 24 with gas A is sealed by a seal 41 extending between the low circumference of the bellows 40 and the housing 30. The interior of the bellows 40 is in fluid communication with the fluid line 16 leading to the right blood pump 12.

The left blood pump 11 may also include a venting means 42 for venting a third volume of gas C located between the housing 30 and the bellows 40 are above the seal 41. In the illustrative embodiment shown in FIG. 2, the venting means 42 consists of a narrow tube 44 in fluid communication with a resilient flaccid sac 46 for retaining the vented gas.

As stated above, the right blood pump 12 may be either a sac type or rotary type. In the illustrative embodiment shown in FIG. 2, the right blood pump is of a sac type including a housing 48 and a blood sac 50 that, when expanded, stretches to the walls of the housing 48. The inlet and outlet ports 26 and 28 include valves 52 for controlling the flow of blood similar to the left blood pump 11. The fluid line 16 is in fluid communication with the housing 48 to permit the gas displaced from the left blood pump 11 to contact the blood sac 50.

The pump housings 30 and 48, may be made of polysulfone or titanium. The casing for the motor 34 may be made of titanium. The blood sacs 22 and 50 may be formed from polyurethane. The bellows 40 is preferably made of stainless steel.

In operation, as the pusher plate 38 presses against the blood sac 22 of the left blood pump 11, ejecting blood therefrom, a vacuum is created within the gas chamber 24 in the area containing gas A which, in concert with the relatively constant pressure of gas C above bellows 40 provided the resilient flaccid sac 46, causes the bellows 40 to contract. The contraction of the bellows 40 forces the gas B through the fluid line 16 and into the housing 48 contracting the right blood sac 50 to eject blood. Similarly, when the motor 34 draws the pusher plate inward, the blood sac 22 expands for receiving blood while the gas A is forced toward the bellows 40 to refill the vacuum area. Concurrently with the blood sac 22 being filled with blood, the blood sac 50 also fills with blood which forces the gas B to be displaced from the right blood pump through the fluid line 16 into the bellows 40. The combination of the displacement of gases A and B causes the bellows 40 to expand. This cyclical operation produces an artificial heart that can fully replace a human heart.

As the bellows 40 is alternately contracted and expanded, a vacuum is created between the bellows 40 and the housing 30. To prevent this vacuum pressure from exerting itself upon the bellows, the gas C in the flaccid sac 46 is alternately drawn into the housing 30 and vented from the housing 30 to eliminate the pressure effects of the contraction and expansion of the bellows 40.

Figure 3:
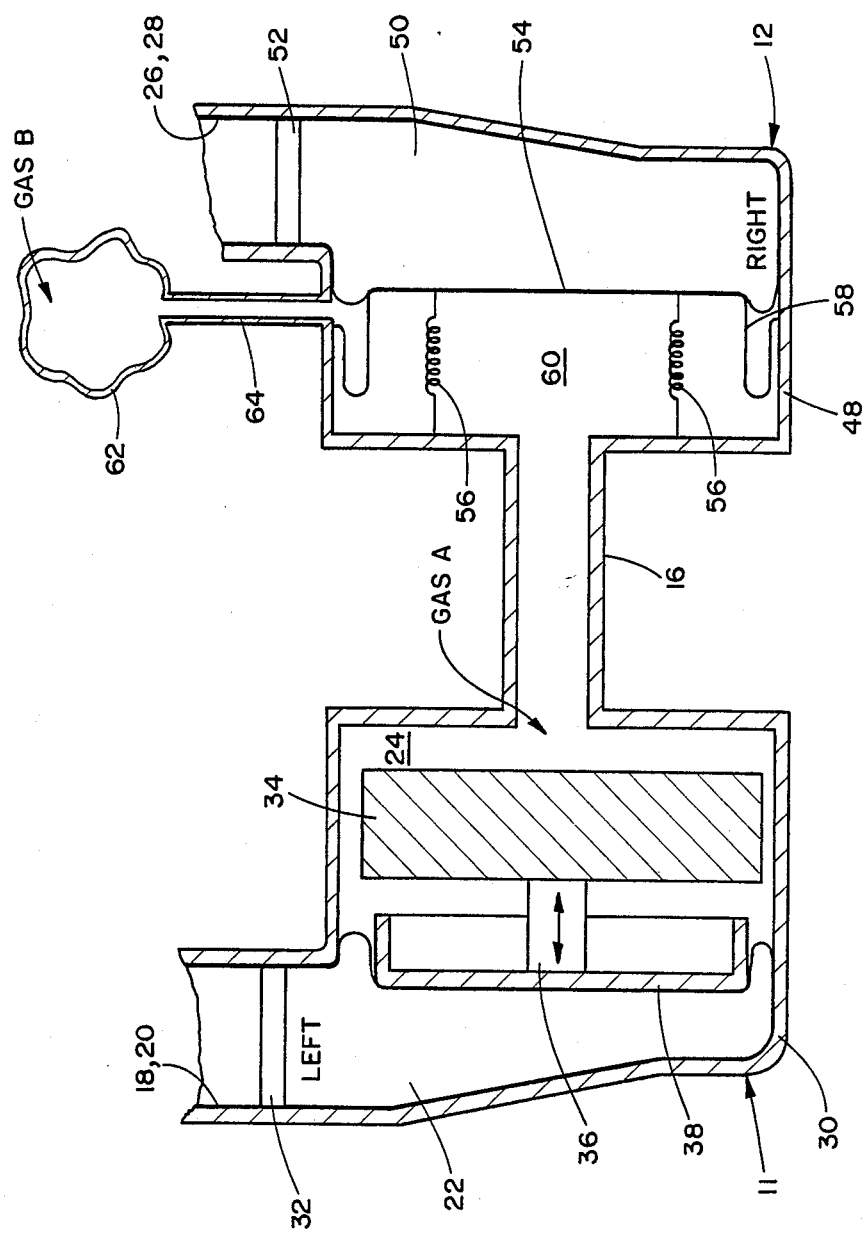
FIG. 3 is a schematic diagram of another embodiment of the artificial heart wherein the right blood pump is spring actuated.

FIG. 3 shows a further embodiment of the present invention wherein the pumping means for the right blood pump 12 includes a pusher plate 54 and a means for causing the pusher plate 54 to reciprocate away from and towards the blood sac 50 for contracting and expanding the sac 50. In the illustrative embodiment shown in FIG. 3, a pair of springs 56, preferably made of stainless steel or titanium, are attached to the pusher plate 54 and the wall of the housing 48. A flexible partition member 58 extends across the diameter of the housing 48 along the pusher plate 54, thereby defining a pumping chamber 60. The partition member 58 may be a rolling diaphragm as shown in the embodiment of FIG. 3 or alternatively, a bellows may be utilized. The diaphragm is preferably made of polyurethane or butyl rubber. The pumping chamber 60 is in fluid communication with the fluid line 16. A flaccid sac 62 is in fluid communication with the space within the housing 48 between the partition 58 and the sac 50, through a narrow tube 64.

In operation, as the pusher plate 38 is extended to contract the left blood sac 22, a vacuum is created within the gas chamber 24 drawing gas A from the right blood pump 12, through the fluid line 16, into the left blood pump 11. The displacement of the gas into the left blood pump 11 causes the springs 56 to compress, drawing the pusher plate 54 towards the fluid line 16 and allowing the sac 50 to fill with blood. When the left blood pump 11 is receiving blood and the pusher plate 38 is moving towards the motor 34, the gas A is forced through the fluid line 16 into the right blood pump 12, thereby forcing the pusher plate 34 to contract the sac 50 to expel blood. The energy stored in the compressed springs 56 is released as the gas is displaced from the gas chamber 24 into the pumping chamber 60 and assists the movement of the pusher plate to contract the sac 50. A gas B is located in the flaccid sac 62 and is alternately discharged into the housing 48 and vented back into the sac 62 to maintain a zero pressure within the housing 48.

Figure 4:
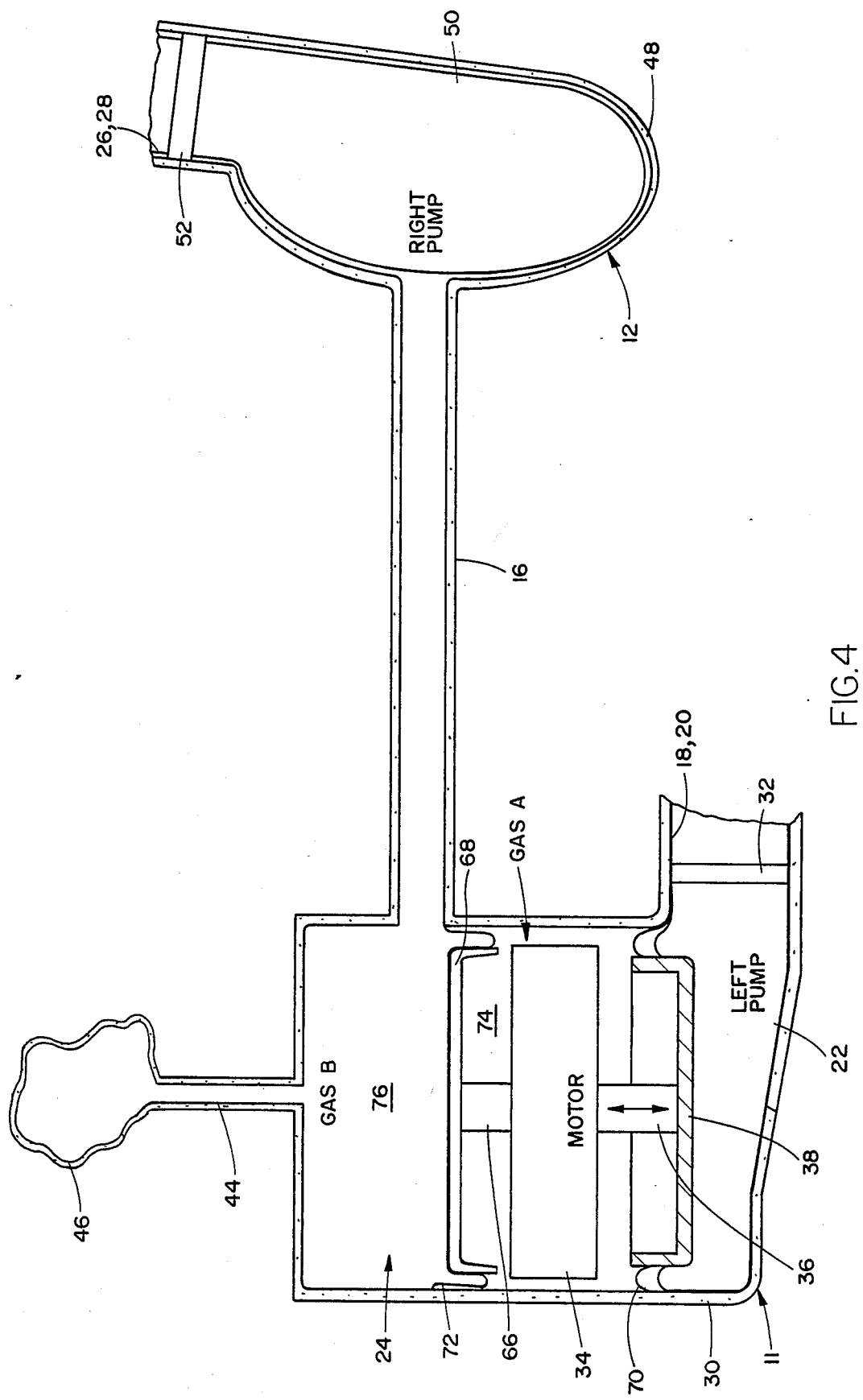
FIG. 4 is a schematic diagram of a further embodiment of the artificial heart wherein the motion translating means includes a rolling diaphragm.

FIG. 4 shows a further embodiment of the artificial heart of the present invention similar to the embodiment shown in FIG. 2 wherein the motor 34 includes an extension shaft 66 attached to the output shaft 36. The extension shaft 66 extends from the motor 34 in the opposite direction from the output shaft 36. A pusher plate 68 is attached to the extension shaft 66. The output shaft 36 and the extension shaft 66 both move in unison in the same direction, thereby causing the pusher plate 38 and pusher plate 68 to also move in the same direction. A flexible partition member 70 is attached to pusher plate 38 across the diameter of the housing 30 and a flexible partition member 72 is attached to the pusher plate 68 across the diameter of the housing 30. As shown in the illustrative embodiment of FIG. 4, the partition members 70 and 72 are rolling diaphragms. However, as mentioned above, bellows may also be used. The partition members 70 and 72 divide the housing 30 into a fixed gas chamber 74 defined between the partitions 70 and 72, and a displaceable gas chamber 76 defined between the partition 72 and the housing 30. The fluid line 16 is in fluid communication with the displaceable gas chamber 76.

In operation, as the motor 34 causes the pusher plate 38 to contract the left blood sac 22, the pusher plate 68 also moves towards the left blood sac 22, thereby creating a vacuum in the area containing the gas B drawing the gas B through the fluid line 16 into the gas chamber 76, causing the blood sac 50 to expand and fill with blood. Similarly, when the left blood pump sac 22 is filling with blood, the pusher plate 68 moves to decrease the volume of gas chamber 76 which displaces the gas B through the fluid line 16 into the housing 48 of the right blood pump 12, thereby contracting blood sac 50 to expel blood. A gas A is located within the fixed gas chamber 74 having a slight vacuum therein to provide a pulling effect upon the diaphragms 70 and 72 to help secure the diaphragms to the pusher plates 38 and 68, respectively.

The flaccid sac 46 in the embodiment shown in FIG. 4 allows for a different volume of blood to be pumped by the left and right blood pumps. The right pump is located within the lung circuit which typically pumps less blood than the left pump located within the systemic circuit. The amount of movement of the pusher plates 38 and 68 is that required to actuate the left pump 11, which may displace more gas B than is required to actuate the right blood pump 12. The flaccid sac 46 receives and expels the amount of gas above that needed to activate the right blood pump 12. In addition, the sac 46 limits the vacuum created in the chamber 24 to prevent damage to the diaphragm 72 or the blood sac 50.

The artificial heart of the present invention provides a heart having two compact blood pumps connected by a fluid line that will permit spatial separation of the left and the right blood pumps within the body. Often, there will be inadequate space in the chest for both the pumping chambers, and the present artificial heart provides the flexibility to permit implantation to conform to the individual needs of the patient. When the artificial heart is being implanted, the surgeon may place one blood pump in the chest and the other blood pump in the abdomen. Alternatively, both pumps may be placed in the chest but in separate areas, such as the upper left quadrant and the lower right quadrant.

Figure 5:
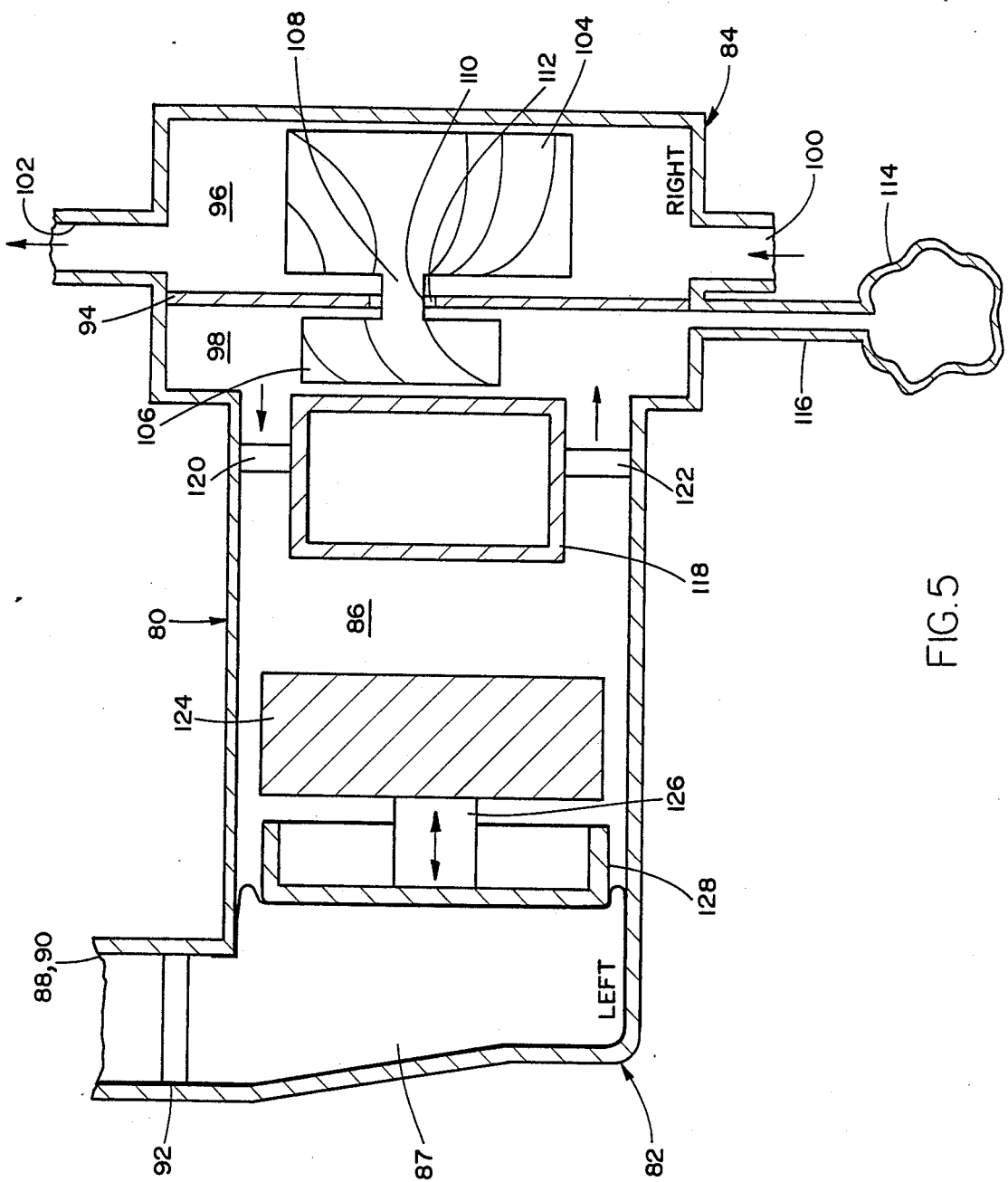
FIG. 5 is a further embodiment of the artificial heart shown as an integral unit.

Nevertheless, the system of the present invention can work extremely well within an artificial heart having a single housing enclosure of unitary construction. The embodiment shown in FIG. 5 schematically shows such an integral unit. However, it should be noted that the system shown in FIG. 5 will also operate with separate blood pumps being interconnected by a fluid line.

The artificial heart shown in FIG. 5 includes a pump enclosure 80 having a left blood pump 82, a right blood pump 84 and a gas chamber 86 defined between the left and right blood pumps 82 and 84. The left blood pump 82 includes a flexible blood sac 87 and inlet and outlet ports 88 and 90 controlled by valves 92 for the continuous flow of blood. The right blood pump is a centrifugal or shear flow pump having a central wall 94 dividing the right blood pump 84 into a blood chamber 96 and a rotary gas chamber 98. The right blood pump 84 includes a blood inlet port 100 and a blood outlet port 102 in fluid communication with the blood chamber 96 to provide access for the flow of blood in and out of the blood pump 84. An impeller 104 is located within the blood chamber 96 and an impeller 106 is located within the rotary gas chamber 98. The impellers 104 and 106 are connected therebetween by a shaft member 108 that extends through a central aperture 110 in the wall 94. The impeller members 104 and 106 may be made of pyrolytic carbon. A bearing or magnetic coupling 112 is located within the aperture 110 to permit the shaft member 108 to freely rotate therein. The right blood pump 84 includes a resilient flaccid sac 114 in fluid communication with the rotary gas chamber 98 through a narrow tube 116.

A centrally located frame member 118 is located between the gas chambers 98 and 86 with valve members 120 and 122 being attached to the frame member 118 and the walls of the enclosure 80 on opposite sides of the frame 118. The valve 120 only permits gas flow in a direction from the chamber 98 into the chamber 86, while the valve 122 only permits gas flow in a direction from the chamber 86 into the chamber 98, which drives and turns the impeller 106 in one direction. A motor 124 having an output shaft 126 and a pusher plate 128 attached thereto is located within the chamber 86, which operates to contract and expand the blood sac 87 of the left blood pump 82.

In operation, as the pusher plate 128 moves to contract the left blood sac 87, a vacuum is created within the gas chamber 86 which draws gas from the flaccid sac 114 over the impeller 106 and through the valve 120, thereby turning the impeller 104 which works to expel blood from the right blood pump 84. Similarly, as the pusher plate moves in the opposite direction to expand the blood sac 87, the gas in chamber 86 is displaced through the valve 122 and then flows through the path of least resistance either passing directly over the impeller 106 or flowing into the flaccid sac 114 to expand the latter. In operation, a portion of the gas will pass directly over the impeller 106 to drive the pump, and a portion of the gas will expand the flaccid sac 114 to store energy thereby. The stored energy is used later as the flaccid sac contracts to continue pumping blood, which continues until all the stored energy is dissipated or until the next cycle of operation of the pump.

Thus, the system of the present invention which utilizes the displaced volume of gas from the left blood pump to power the low pressure right blood pump provides an artificial heart that is both decreased in size and weight and is energy efficient. In addition, the artificial heart permits the spatial separation of the left and the right blood pumps which will facilitate the implantation of the heart into the chest.

While illustrative embodiments of the subject invention have been described and illustrated, it is obvious that various changes and modifications can be made therein without departing from the spirit of the present invention which should be limited only by the scope of the appended claims.

What is claimed is:

1. An artificial heart, comprising:
   a. a left blood pump including a pump housing, a flexible blood sac, a fluid chamber containing a fluid, and a motion translating means for contracting and expanding said flexible blood sac, said motion translating means also being operative to displace the fluid located within said fluid chamber;
   b. a right blood pump coupled to said fluid chamber of said left blood pump by a fluid line, said right blood pump including a pump housing, a blood chamber, and a fluid powered pumping means for causing blood to enter and exit said blood chamber, said fluid line being generally external to and linking said right and left pump housings, said fluid powered pumping means being driven solely by the fluid displaced through said fluid line by said motion translating means of said left blood pump, such that the fluid displaced through said fluid line by said motion translating means of said left blood pump cyclically drives the fluid powered pumping means of said right blood pump.

2. The artificial heart of claim 1 wherein said motion translating means includes an electric motor having a first reciprocating pusher plate connected to an output shaft of said motor, said pusher plate being in contact with said blood sac.

3. The artificial heart of claim 1 wherein said motion translating means includes a bellows being in fluid communication with said fluid line for displacing the fluid through said fluid line.

4. The artificial heart of claim 1 wherein said motion translating means is located within said left pump housing.

5. The artificial heart of claim 1 wherein said motion translating means is located within said fluid chamber.

6. The artificial heart of claim 1 wherein said fluid is a gas.

7. The artificial heart of claim 1 wherein said fluid is a liquid.

8. The artificial heart of claim 6 wherein said gas is selected from the group consisting of $SF_6$, He and 9. The artificial heart of claim 6 wherein said fluid chamber comprises a bellows containing a first gas and in which the contracting and expanding of said left blood pump cyclically displaces a second gas causing said bellows to alternately contract and expand, thereby cyclically displacing the first gas through said fluid line for alternately contracting and expanding said right blood pump.

10. The artificial heart of claim 9 further including a venting means for alternately venting a third gas within said left pump housing as said bellows is expanded and contracted.

11. The artificial heart of claim 10 wherein said venting means includes a flaccid sac in fluid communication with said housing adjacent said bellows.

12. The artificial heart of claim 1 wherein said right blood pump includes a flexible blood sac defining said blood chamber.

13. The artificial heart of claim 12 wherein said pumping means includes a pusher plate adjacent said right blood sac and a reciprocating means for alternately contracting the expanding said blood sac.

14. The artificial heart of claim 13 wherein said reciprocating means includes at least one spring means attached to said housing and said pusher plate, said spring means being alternately compressed and released by the displacement of the fluid through said fluid line.

15. The artificial heart of claim 14 wherein said pumping means includes a flexible partition member connected between said pusher plate and said housing thereby defining a alternately expandable and contractable pumping chamber for the receipt and discharge of the displaced fluid from said left blood pump.

16. The artificial heart of claim 15 wherein said fluid is a gas.

17. The artificial heart of claim 16 wherein said partition member is a diaphragm.

18. The artificial heart of claim 16 wherein said partition member is a bellows.

19. The artificial heart of claim 14 wherein said right blood pump includes a venting means for alternately venting and replacing a gas within said right pump housing as said pumping chamber is expanded and contracted.

20. The artificial heart of claim 19 wherein said venting means includes a flaccid sac in fluid communication in the said right pump housing.

21. The artificial heart of claim 2 wherein said motor includes a shaft extension member attached to said output shaft extending into said pump housing opposed from said output shaft, a second reciprocating pusher plate connected to said shaft extension member, said first and second pusher plates reciprocating in the same relative direction, and a flexible partition member secured to said second pusher plate and said pump housing, thereby dividing said fluid chamber into a fixed fluid chamber between said pusher plates and a displaceable fluid chamber between said second pusher plate and said pump housing, said fluid line being in fluid communication with said displaceable fluid chamber.

22. The artificial heart of claim 21 further including a second flexible partition member secured to said first pusher plate and said pump housing.

23. The artificial heart of claim 22 wherein said fluid is a gas.

24. The artificial heart of claim 23 wherein said partition member is a diaphragm.

25. The artificial heart of claim 23 wherein said partition member is a bellows.

26. The artificial heart of claim 22 wherein said left blood pump housing includes a venting means in fluid communication with said displaceable gas chamber for alternately venting and replacing the gas within said displaceable gas chamber after said right blood pump is contracted and expanded.

27. The artificial heart of claim 26 wherein said venting means includes a flaccid sac.

28. The artificial heart of claim 27 wherein said venting means includes a thin-walled tube.

29. The artificial heart of claims 1, 2, or 27 herein said right and left blood pumps are spatially separated.

30. The artificial heart of claim 1, wherein said left blood pump housing has blood inlet port and a blood outlet port and a valve means within each inlet and outlet port, said left blood pump being motor actuated for expanding and contracting said blood sac, and said right blood pump being spatially separated from said left blood pump and including a blood inlet port and blood outlet port and a valve means within each inlet and outlet port.

* * * * *

UNITED STATES PATENT AND TRADEMARK OFFICE
CERTIFICATE OF CORRECTION

PATENT NO. : 4,820,300
DATED : April 11, 1989
INVENTOR(S) : William S. Pierce, et al.

It is certified that error appears in the above-identified patent and that said Letters Patent is hereby corrected as shown below:

Column 7, line 47, Claim 8: "He and" should read as --He and Ar.

Column 8, line 18, Claim 19: "claim 14" should read as --claim 16--

Column 8, line 57, Claim 29: "herein" should read as --wherein--

Column 8, line 61, Claim 30: "has blood" should read as --has a blood--

Signed and Sealed this

Thirteenth Day of February, 1990

Attest:

JEFFREY M. SAMUELS

*Attesting Officer*   *Acting Commissioner of Patents and Trademarks*